United States Patent [19]

Wong

[11] Patent Number: 5,079,422

[45] Date of Patent: Jan. 7, 1992

[54] FIRE DETECTION SYSTEM USING SPATIALLY COOPERATIVE MULTI-SENSOR INPUT TECHNIQUE

[75] Inventor: Jacob Y. Wong, Santa Barbara, Calif.

[73] Assignee: Gaztech Corporation, Goleta, Calif.

[21] Appl. No.: 583,234

[22] Filed: Sep. 13, 1990

Related U.S. Application Data

[63] Continuation-in-part of Ser. No. 503,215, Apr. 12, 1990, which is a continuation-in-part of Ser. No. 403,587, Nov. 6, 1989, Pat. No. 5,026,992.

[51] Int. Cl.$^5$ ............................................. G08B 17/117
[52] U.S. Cl. .................................... 250/343; 250/340; 250/349; 340/577
[58] Field of Search ............... 250/339, 340, 341, 343, 250/345, 346, 349; 340/632, 577, 578

[56] References Cited

U.S. PATENT DOCUMENTS

| | | | |
|---|---|---|---|
| 4,160,163 | 7/1979 | Nakauchi | 250/340 |
| 4,390,869 | 6/1983 | Christen et al. | 340/632 |
| 4,694,172 | 9/1987 | Powel et al. | 250/339 |
| 4,745,399 | 5/1988 | Kimura | 340/632 X |
| 5,026,992 | 6/1991 | Wong | 250/343 |

FOREIGN PATENT DOCUMENTS 2190777 11/1987 United Kingdom ............... 340/577

*Primary Examiner*—Constantine Hannaher
*Attorney, Agent, or Firm*—Daniel C. McKown

[57] ABSTRACT

A system for detecting fires uses at least two carbon dioxide sensors positioned at spaced locations in a room. Each sensor produces an electrical output signal representative of the carbon dioxide concentration in its vicinity. A computer calculates the ratio of the concentration sensed by each sensor to the concentration sensed by each of the other sensors, and any imbalance in the distribution of carbon dioxide will be reflected in these ratios. Random variations prevent the ratios from being equal, and the magnitude of the random variations is quantized by calculating the standard deviation of the ratios. The ratios are then normalized and compared to a threshold level that corresponds to a chosen false alarm rate.

22 Claims, 6 Drawing Sheets

| | R₁ | R₂ | R₃ | R₄ | ... |
|---|---|---|---|---|---|
| R₁ | | $R_2/R_1$ | $R_3/R_1$ | $R_4/R_1$ | |
| R₂ | $R_1/R_2$ | | $R_3/R_2$ | $R_4/R_2$ | |
| R₃ | $R_1/R_3$ | $R_2/R_3$ | | $R_4/R_3$ | |
| R₄ | $R_1/R_4$ | $R_2/R_4$ | $R_3/R_4$ | | |

FIRE DETECTION SYSTEM USING SPATIALLY COOPERATIVE MULTI-SENSOR INPUT TECHNIQUE

RELATED PATENT APPLICATIONS

This application is a continuation-in-part of U.S. Pat. application Ser. No. 07/503,215 filed Apr. 2, 1990 for "Rapid Fire Detector", which in turn was a continuation-in-part of U.S. Pat. application Ser. No. 07/403,587 filed Nov. 6, 1989 for "Spectral Ratioing Technique for NDIR Gas Analysis Using a Differential Temperature Source", now U.S. Pat. No. 5,026,992. Priority based on the filing dates of these two earlier applications is claimed for material common to them and the present invention. The earlier applications in their entirety are incorporated herein by reference.

In Ser. No. 07/403,587, the present inventor disclosed an instrument having no moving parts and using a differential temperature source and dual pass band filter to determine the concentration of a gas in a sample chamber. Methane was used as an exemplary gas because that gas is often encountered in underground mining operations.

In application No. 07/503,215, the present inventor applied the spectral ratioing technique to a sensor for detecting carbon dioxide gas. That sensor was compact, sensitive, and had no moving parts, thereby making it attractive for the early detection of fires.

In this application, the present inventor will show how a number of the carbon dioxide sensors can be deployed within a room in a system that permits earlier and more reliable detection of a fire than is possible when only a single sensor is used.

BACKGROUND OF THE INVENTION

1. Field of the Invention

The present invention is in the field of fire detection and more specifically relates to a system and method using several spaced sensors that measure the concentration of gaseous carbon dioxide for detecting the onset of a fire in a building as early as possible and with a minimum of false alarms.

2. The Prior Art

The fire detectors that are available commercially today fall into three basic classifications, namely flame sensing, temperature sensing, and smoke-sensing. These respond, respectively, to the luminous flame, the heat, and the smoke that almost always accompany fires.

In U.S. Pat. application No. 07/503,215, the present inventor proved the existence of a fourth category, namely carbon dioxide sensors, which are based on the recognition that in most fires, the fuel is organic material which is oxidized in the combustion process with the concomitant production of carbon dioxide.

Typically, flame sensors, temperature sensors, and smoke sensors have been developed and installed as separate stand-alone independent sensors. This may result from the fact that in many applications, such as small rooms in a house, a single sensor is capable of providing a minimal degree of protection. That is, most of the sensors that are sold are installed on a one-per-room or one-per-building basis. Accordingly, less attention was devoted to using more than one sensor per room or per building.

SUMMARY OF THE INVENTION

The present invention is a system for the early detection of a fire in a room or in an unpartitioned building. When used in the system of the present invention, the individual carbon dioxide sensors continue to use their stand-alone fire-detecting capabilities.

What, then, is the advantage of connecting the sensors to a system? The present inventor has discovered that by connecting the sensors into a system, the probability of false alarms can be reduced and earlier detection is made possible.

That is to say, a synergistic effect is obtained through the use of the system, and that two or more sensors are more valuable when connected to the system of the present invention than when they are used separately, without the system.

It is not immediately apparent why this should be so, considering that the sensors retain their stand-alone capability when connected into the system.

In accordance with the present invention there are two main ways in which the synergistic effect is brought about by the system. The first is that the system, unlike an individual sensor, can capitalize on the use of a priori information regarding the expected nature of a fire. Particular examples of a priori information are that the start of a fire is an event which is localized in space and which is sudden in time. Another example of a prior information used by the system is that the carbon dioxide produced by a fire is hot relative to the surrounding air and tends to rise.

The second way in which the system has an advantage over an aggregation of unconnected sensors is that the system has at its disposal an historical database of information regarding the previous outputs of all the sensors and can analyze this information to develop baselines from which the significance of the present outputs of individual sensors can be judged. Examples of this are the use of the outputs of all the sensors to calculate mean values and variances from which the statistical significance of a particular reading can be assessed.

Thus, it is an object of the present invention to exploit both a priori information and the historic database of information generated by the sensors in a system so as to permit earlier detection and reduction of false alarms.

The novel features which are believed to be characteristic of the invention, both as to organization and method of operation, together with further objects and advantages thereof, will be better understood from the following description considered in connection with the accompanying drawings in which a preferred embodiment of the invention is illustrated by way of example. It is to be expressly understood, however, that the drawings are for the purpose of illustration and description only and are not intended as a definition of the limits of the invention.

DETAILED DESCRIPTION OF THE PREFERRED EMBODIMENT

Figure 1:
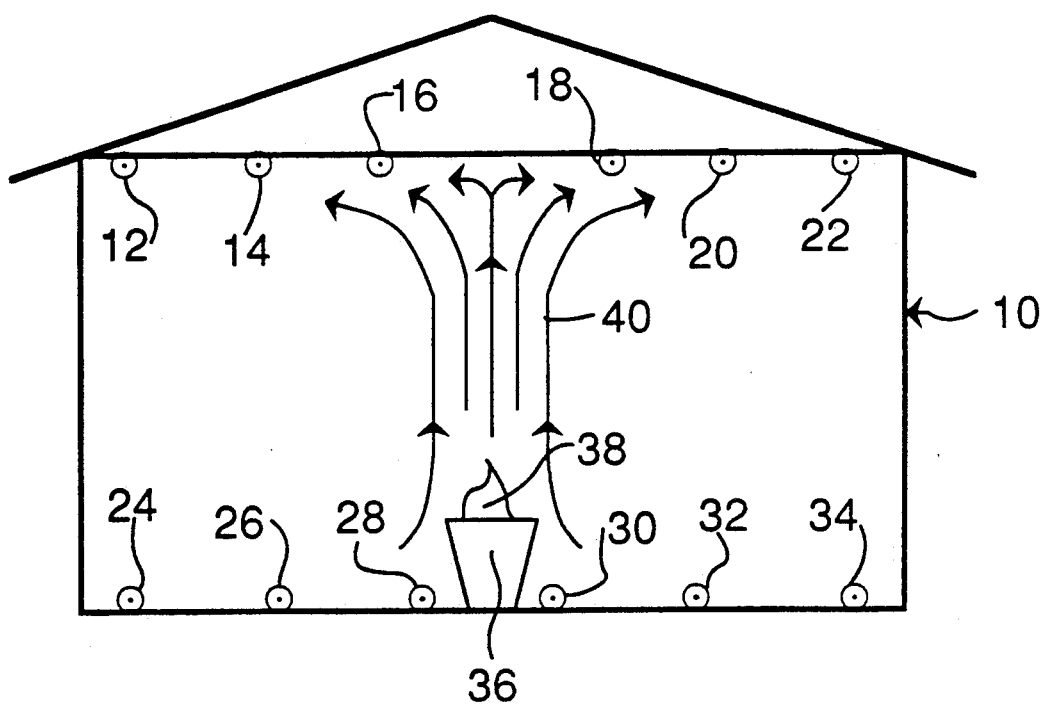
FIG. 1 is a diagram showing a number of sensors distributed throughout a room.

The present invention is a fire detection system that permits earlier detection of fires with a reduced false alarm rate compared to the results that would be obtained if the system were not used. As shown in FIG. 1, the system is intended for use in a large room or an unpartitioned building 10, and in accordance with the invention a number of sensors 12, 14, 16, 18, 20, and 22 are mounted in the upper part of the room 10, typically on the ceiling. A number of other sensors 24, 26, 28, 30, 32, and 34 are mounted at various locations in the lower portion of the room, typically on or near the floor. In accordance with the invention, any number of sensors can be placed in the upper portion of the room, and a different number may be placed in the lower portion of the room. The sensors are of the type described in U.S. Pat. application Ser. No. 07/503,215, and the sensors produce electrical signals that represent, respectively, the concentration of carbon dioxide gas in the sample chamber within the sensor and the rate of change of that concentration. Typically, a fire starts in a waste receptacle 36 and a flame 38 may be produced. Hot gases produced by the fire move upward along convection paths of which the path 40 is typical.

Figures 2, 3:
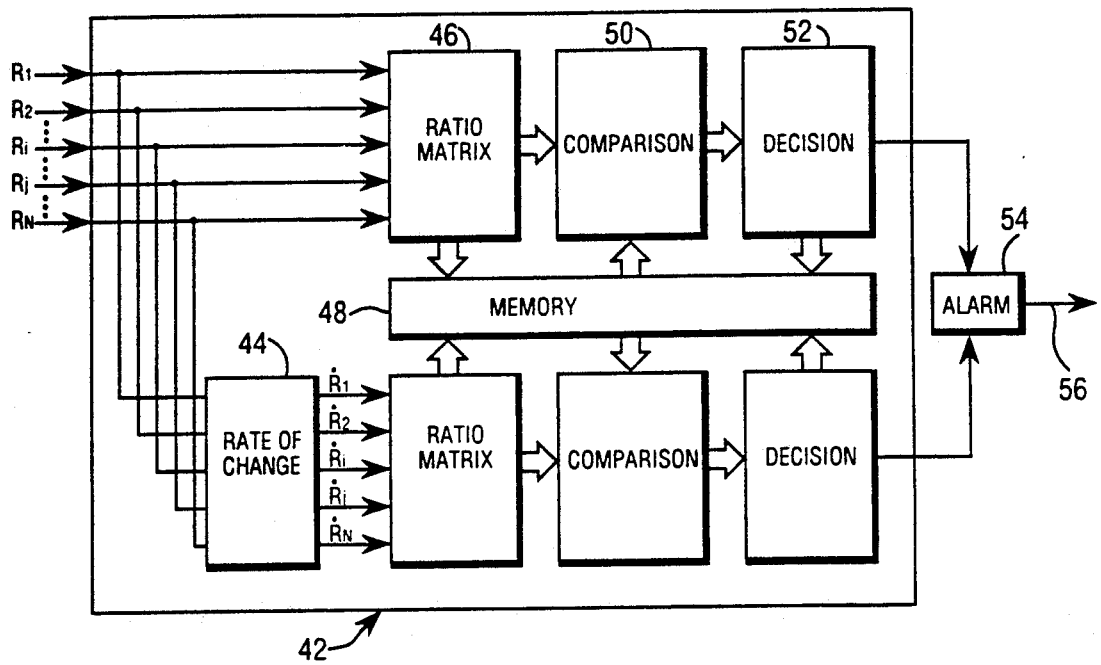
FIG. 2 is a block diagram showing a portion of the system in a preferred embodiment of the present invention.
FIG. 3 is a matrix of the type used in the preferred embodiment of FIG. 2.

In the following discussion, the electrical signals produced by sensors 1, 2, ... i, ... j, ... N are denoted by $R_1$, $R_2$... $R_i$... $R_j$, ... $R_N$, respectively. The instantaneous rates of change of these variables are denoted by $\dot{R}_1$, $\dot{R}_2$, ... $\dot{R}_i$, ... $\dot{R}_j$, ... $\dot{R}_N$. The signals representing the carbon dioxide concentrations are applied, in accordance with a first preferred embodiment of the invention shown in FIG. 2, to a computer 42 that includes a portion 44 that calculates the instantaneous rate of change $\dot{R}_i$ of these signals. In an alternative embodiment, the rates of change $\dot{R}_i$ are determined at the respective sensors, and the signals representing the rates of change are applied to the computer 42 in addition to the signals representing the concentration. The computer 42 includes circuitry 46 for calculating the ratio of each of the signals $R_i$ to each of the other signals $R_j$. The resulting matrix is shown in FIG. 3.

When there is no fire, one would expect the ratios to be very close to 1.00.

Since the ratios are derived, respectively, from every possible combination of two sensors, the ratios embody all of the available information regarding any imbalances that may be present in the concentration of carbon dioxide gas.

In accordance with the present invention, the computer 42 makes full use of certain a priori information; namely, that when a fire first starts, it is localized in space and it produces a change in the carbon dioxide concentration that is sudden in time. It will now be seen how the computer 42 utilizes this a priori information.

Using FIG. 1 as an example, the presence of the fire will cause a rapid increase in the concentration of carbon dioxide in the neighborhood of the sensors 16 and 18, but will have negligible effect on the sensors 28 and 30. Consequently, all of the ratios of FIG. 3 that are derived from the information from sensors 16 and 18 will rapidly depart from unity. Certain other ratios, such as between the sensor 12 and the sensor 24 may not initially show any change.

It is important to note that the system of the present invention makes no assumptions with regard to where the fire will be located. As soon as an imbalance in the distribution of carbon dioxide has been detected by any of the sensors, the imbalance will show up in one or more of the ratios in the ratio matrix of FIG. 3.

In the first preferred embodiment of the invention, the ratio matrix of FIG. 3 is calculated periodically; for example, every 10 seconds. The entire calculated matrix is stored in the memory 48 of the computer.

Every 10 seconds a new ratio matrix is calculated, and the new ratio matrix is compared in the comparator 50 with a matrix that is an average of the matrices that have been stored in the memory 48. This comparison enables the computer 42 to make use of the a priori information that a fire will produce a rather swift change in some of the ratios. The difference in the ratios is applied to the decision circuit 52, and if that circuit determines that some of the ratios have changed significantly, the decision circuit 52 will send a signal to the alarm signal generator 54 which then produces an alarm signal on the line 56. FIG. 2 shows a similar processing scheme for the rates of change $\dot{R}_i$. The operation of the decision circuits 52 will be described in greater detail in connection with FIG. 4.

Figure 4:
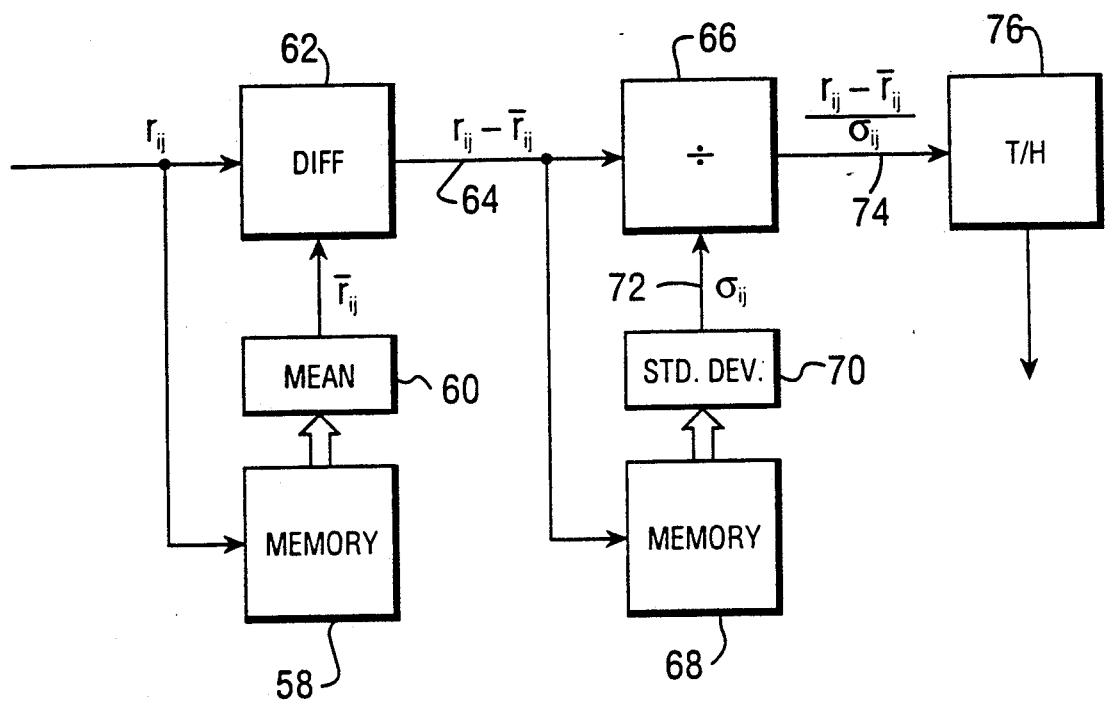
FIG. 4 is a block diagram showing portions of the system of FIG. 2 in greater detail.

Let $r_{ij}$ equal the ratio $R_i/R_j$, where $R_i$ and $R_j$ are sensed at the same instant of time. FIG. 4 illustrates the calculation carried out by the computer for each of the ratios in the ratio matrix of FIG. 3. Successive values of $r_{ij}$ are stored in the memory 58 at the end of each sampling interval. These successive values of $r_{ij}$ are called up from memory by the circuit 60, which averages a number of them to produce a time-averaged value $r_{ig}$. The circuit 62 then subtracts the mean value from the newly measured value $r_j$. This difference signal on the line 64 is then applied to the circuit 66 and also to the memory 68. The memory 68 retains a number of such deviations from the mean, and from them the circuit 70 calculates an estimate of the standard deviation on the line 72. The deviation on the line 64 is divided by the standard deviation on the line 72 by the circuit 66 to obtain the normalized deviation on the line 74.

The advantage of calculating the normalized deviation on the line 74 is that, assuming $r_j$ is normally distributed, then the probability of the normalized deviation exceeding a particular numerical value is known. For example, the probability that the deviation will exceed +2.5 is 0.621%. Thus, there is less than 1% probability that such a large reading of the normalized deviation would be caused by random fluctuations. The probability is actually the false alarm rate. Accordingly, if such a deviation is observed, the computer would be justified in attaching a high degree of significance to the occurrence and in assuming that it is caused by a fire rather than by a random fluctuation, i.e., rather than just a false alarm. In the threshold circuit 76, the normalized deviation on the line 74 is compared with a preset number obtainable from standard statistical tables, and if the preset number is exceeded, an alarm signal is generated.

The first preferred embodiment of FIGS. 2, 3 and 4 illustrates a number of salient aspects of the present invention. First, the present invention makes use of the a priori information that a fire will cause spatial variations in the concentration of carbon dioxide. This is taken into account in the present invention by the ratio matrix in which the concentration at each sensor location is compared with the concentration at all of the other sensor locations. If there were no fire, all of the ratios would be close to 1.00, reflecting a relatively uniform distribution of carbon dioxide. When a fire breaks out, some of the ratios will rapidly become greater than 1.00 and their reciprocals will become less than 1.00 and will be ignored by the computer. Thus, the system of the present invention takes advantage of the a priori knowledge that in its early stages, a fire produces a non-uniform spatial distribution of the carbon dioxide in the room.

Second, the system of the present invention takes advantage of the a priori knowledge that in its early stages a fire alters the concentration in the vicinity of one or more particular sensors in a sudden and drastic manner. Thus, the system of the present invention monitors the temporal stability of each of the ratios by the technique illustrated in FIG. 4, which provides a rational basis for setting the threshold levels.

In a variation of the first preferred embodiment, differences in the readings provided by the sensors are used instead of the ratios, and instead of a ratio matrix, one would have a difference matrix.

Third, inherent in the system of the present invention is the concept that through the use of a computer, a valuable database can be accumulated. This historical data is utilized by the system in determining the significance of the incoming sensor readings. This, in turn permits all diurnal and weekly variations to be discounted.

The memory requirement for the computer is well within present day capabilities. For example, if 10 sensors are used and each sensor transmits 2 bytes every 10 seconds, a week's data will require only 1.2 megabytes of memory.

Thus, in addition to its ability to make use of a priori information, the system of the present invention develops a database which permits a more knowledgeable assessment of the significance of the incoming sensor readings.

Figure 5:
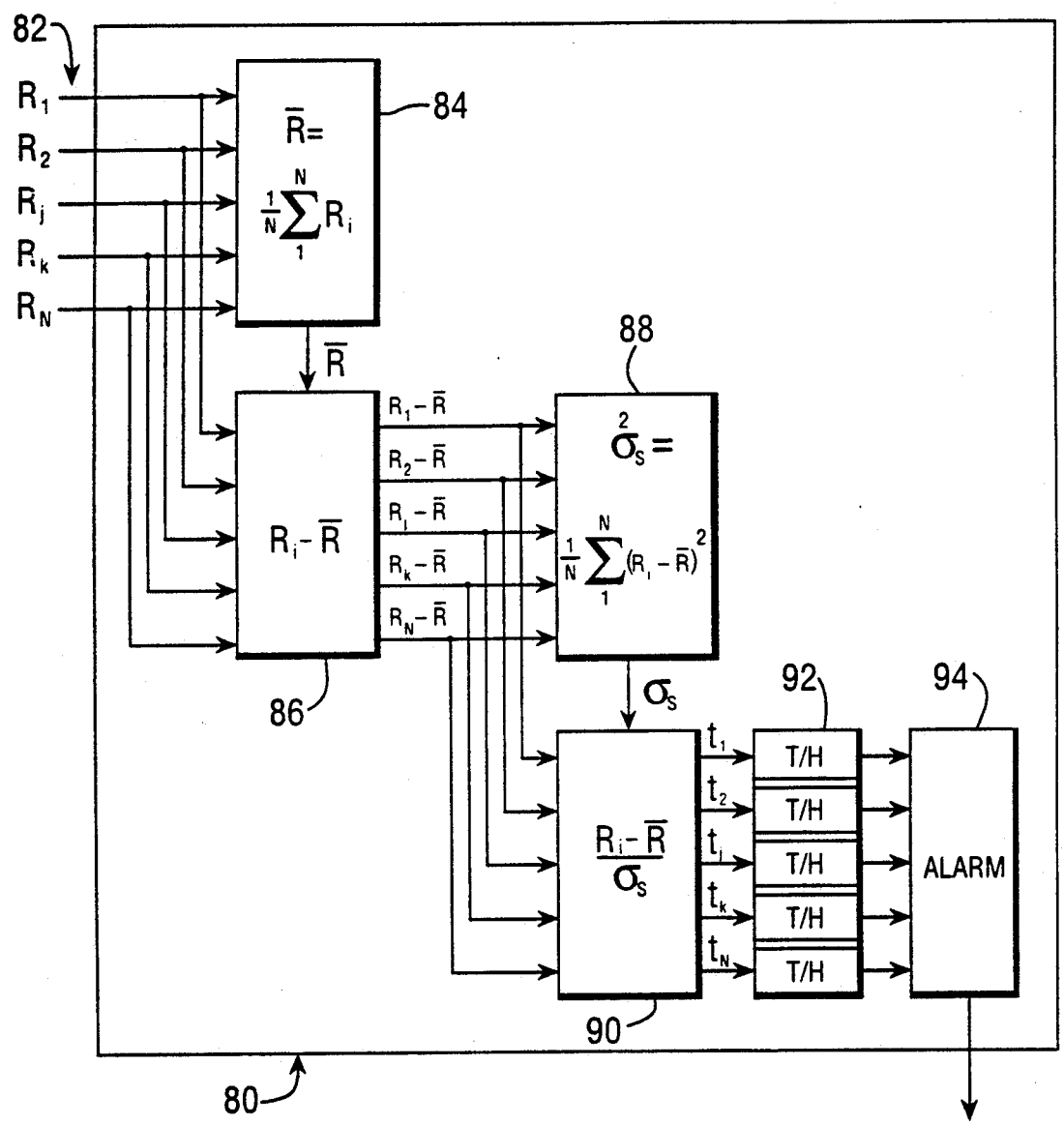
FIG. 5 is a block diagram showing the system in a second preferred embodiment of the present invention.

FIG. 5 shows a second preferred embodiment for evaluating the spatial variations in the concentration of carbon dioxide in a room. The readings from the N sensors are brought into the computer 80 on the lines 82 and are applied to the circuit 84 and to the circuit 86. The circuit 84 calculates the average value of the concentration and applies the average value $\overline{R}$ to the circuit 86, which calculates the amounts by which each of the readings departs from the average value $\overline{R}$. These deviations are applied both to the circuit 88 and to circuit 90. The circuit 88 calculates the standard deviation $\sigma_s$, and the circuit 90 divides each of the deviations by the standard deviation to obtain the normal deviations $t_1 ... t_N$.

Assuming there is no fire, the incoming readings $R_1 ... R_N$ will, in practice, not be identical, and the factors causing the readings not to be identical may never be identified. Perhaps there are in fact small variations in the concentration of carbon dioxide, or perhaps the sensors differ in their accuracy, or perhaps there are transmission losses between the sensor and the computer. The variations among the readings caused by these unidentified factors are referred to as random fluctuations.

The probability that such random fluctuations would cause one of the normal deviations $t_j$ to exceed a particular numerical value can be calculated on the assumption that the random fluctuations have a Normal statistical distribution. As discussed above, if the magnitude of a normal deviation $t_j$ is such that it would be unlikely to occur as a result of the random fluctuations, then the assumption is made that its magnitude is caused by a fire. The normal deviations are compared with preset numerical values in the threshold circuits 92, and if the deviation exceeds the threshold value, an alarm signal is generated by the circuit 94.

It should be stressed that the computer of FIG. 5 analyzes only the spatial variations in the concentration of carbon dioxide in the room. It compares the concentration at each sensor location with the average sensed concentration, and all this is done at a particular time.

Figure 6:
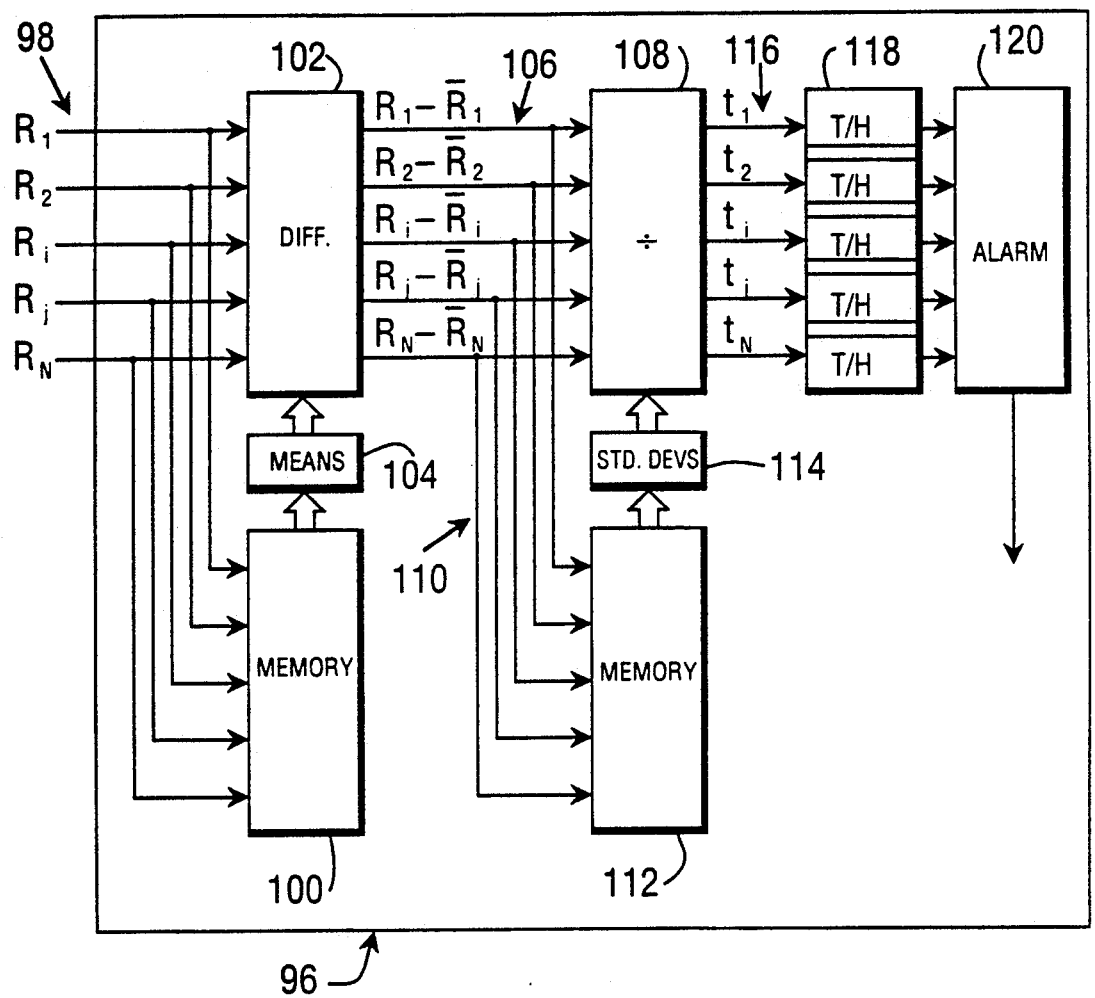
FIG. 6 is a block diagram showing the system in a third preferred embodiment of the present invention.

In contrast, the computer of FIG. 6, which is a third preferred embodiment, compares the concentration reading of each sensor with the average reading of that same sensor over a period of time. If the current reading of that sensor deviates from its long-term average reading by a large amount which cannot be explained as a random fluctuation, then the assumption is made that the large reading is caused by a fire. In the computer of FIG. 6, in contrast to that of FIG. 5, the averages are taken over a period of time for a particular sensor, while in FIG. 5 the averages are taken over the ensemble of sensors at a particular time. The computer of FIG. 5 analyzes the spatial distribution of carbon dioxide in the room, while the computer of FIG. 6 analyzes the temporal variations in carbon dioxide at each sensor location.

The signals from the sensors, representing the concentration of carbon dioxide are brought into the computer 96 of FIG. 6 on the lines 98, and are applied to the memory 100 and to the difference circuit 102. Already stored in the memory 100 are the successive readings for each of the sensors at each sampling time in the past. For each of the sensors, a predetermined number of readings are averaged to arrive at an average reading for that sensor; these averages are calculated by the circuit 104 and applied to the difference circuit 102, which calculates the difference between the incoming reading of a sensor and its average reading in the recent past. The resulting differences are applied via the lines 106 to the circuit 108, and via the lines 110 to the memory 112. Differences obtained in previous sampling intervals have already been stored in the memory 112, and these are applied to the circuit 114 which calculates a standard deviation for each of the channels.

The differences on the lines 106 are divided by their corresponding standard deviations in the circuit 108 to obtain the normal deviations on the lines 116. These normalized deviations are applied to the threshold circuit 118 which compares their magnitudes with preset numbers that correspond to the probability levels desired. If any of the thresholds in the circuit 118 is exceeded, the alarm circuit 120 generates an alarm signal.

In a variation of this third preferred embodiment, the readings of the various sensors are compared with their respective readings at an earlier time, typically 24 hours or 168 hours earlier, and the differences are calculated. Next, those differences are fed into the computer of FIG. 6 on the lines 98. In a further embodiment, the instantaneous reading of each sensor is compared with its reading at some time in the past by forming a ratio of the current reading to the past reading. These ratios are then applied to the computer of FIG. 6 on the lines 98 in place of the instantaneous sensor readings. In this way, the computer of FIG. 6 can be employed to compensate for daily or weekly variations in the concentration levels at the various sensors.

Figure 7:
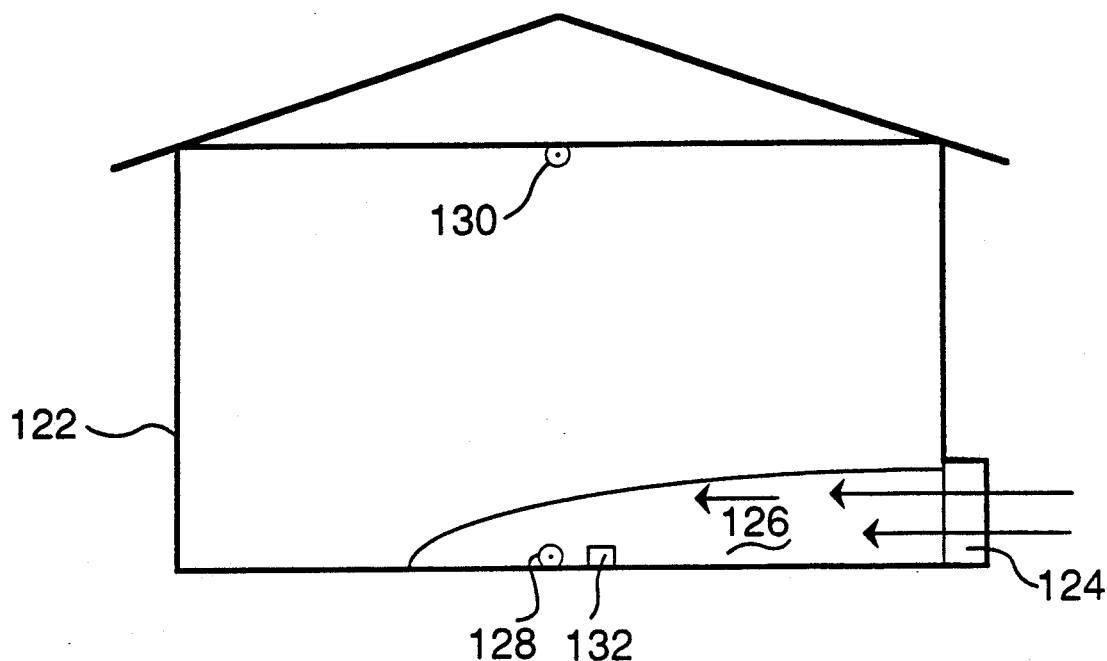
FIG. 7 is a diagram illustrating an alternative embodiment.

A further embodiment is suggested by the situation shown in FIG. 7. The air outside the building 122 is assumed to be colder than the air inside the building. A door 124 is opened, and a mass 126 of cold air flows into the building, as indicated by the arrows. Because it is denser, the mass of cold air sweeps across the floor, displacing the warmer air that originally filled that space.

Owing to the presence of people and other oxygen burners, the concentration of carbon dioxide inside a building is never less than the concentration outdoors. For this reason, the sensor 128 located near the floor may sense a decrease in carbon dioxide concentration as the cold air mass 126 sweeps over it. Meanwhile, the sensor 130 located near the ceiling senses no change in carbon dioxide concentration.

The ratio of the concentration sensed by the sensor 130 to the concentration sensed by the sensor 128 increases just as it would if a fire had started. In this way, the system is deceived into giving a false alarm.

One way to prevent such false alarms is to inhibit the alarm signal if it arises from a situation in which the denominator of an alarm-causing ratio is decreasing. For example, if the signal $R_2$ in the ratio matrix of FIG. 3 is decreasing, thereby causing all of the ratios in the second row of the matrix to increase, any alarm indicated by the ratios in that row should be inhibited. This approach is based on the reasonable premise that a fire is enormously more likely to cause an increase in carbon dioxide concentration than a decrease, at any particular sensor location.

Another way to prevent such a false alarm is to employ other types of sensors to inhibit the alarm. In the above example, a temperature sensor 132 located near the carbon dioxide sensor 128 could be used. The alarm would be inhibited if the sensed temperature decreases. An electrical switch actuated by opening the door could also be used to generate a inhibiting signal.

Figure 8:
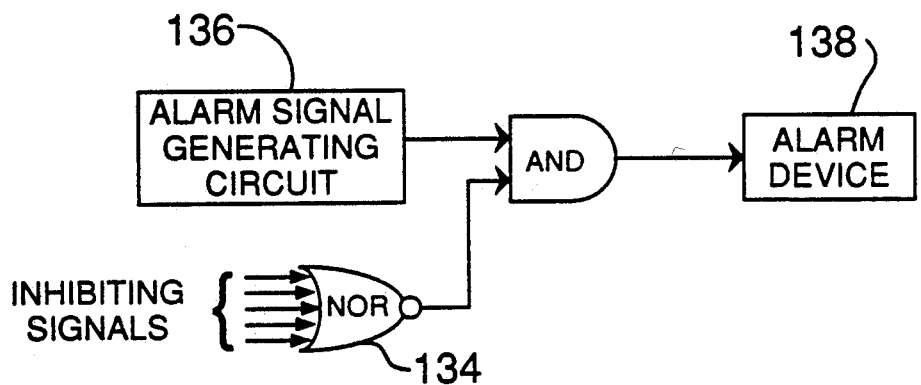
FIG. 8 is an electrical block diagram relating to the alternative embodiment of FIG. 7.

As shown in FIG. 8, inhibiting signals from the auxiliary sensors and from the signal processing circuits are applied through a NOR gate 134 to open the conductive path between the alarm signal generating circuit 136 and the alarm device 138.

It is noteworthy that given sufficient computer memory capacity, all of the embodiments and variations described above can, in principle, be employed simultaneously.

Thus, there has been described a fire detection system that offers improved performance by taking advantage of a priori information and by taking advantage of its database of previous measurements. Among the a priori information is the fact that initially fires are localized in space and that their onset is accompanied by rapid changes in the concentration of carbon dioxide both with respect to space and with respect to time.

From the database developed by the computer portion of the system, it is possible to compare the reading of a sensor with its readings 24 and 168 hours ago so as to permit daily and weekly variations in carbon dioxide concentration to be compensated for.

As a result of its ability to exploit both a priori information and database information, the fire detection system of the present invention can respond more quickly and with greater certainty to sensed changes in the carbon dioxide level.

Finally, the system of the present invention provides a sound statistical rationale for determining threshold levels in accordance with a desired probability of false alarm.

The foregoing detailed description is illustrative of several embodiments of the invention, and it is to be understood that additional embodiments thereof will be obvious to those skilled in the art. The embodiments described herein together with those additional embodiments are considered to be within the scope of the invention.

What is claimed is:

1. Apparatus for detecting a fire in a room, comprising in combination:
    at least two carbon dioxide sensors positioned at spaced locations in the room, each sensor producing an electrical output signal that represents the concentration of carbon dioxide sensed at the location of the sensor;
    ratio means electrically connected to said at least two carbon dioxide sensors for receiving the electrical output signals and for calculating the ratio of the concentration sensed by each sensor to the concentration sensed by each of the other sensors;
    normalization means responsive to the calculated ratios for producing normalized ratios;
    comparison means for comparing the normalized ratios to a threshold level that in the absence of a fire has only a pre-selected small probability of being exceeded by a normalized ratio; and,
    alarm signal generator means for generating an alarm signal when any of the normalized ratios exceeds the threshold level.

2. The apparatus of claim 1 wherein some of said at least two carbon dioxide sensors are positioned at different elevations within the room.

3. The apparatus of claim 1 wherein said normalization means further include means for calculating the standard deviator of the calculated ratios for a particular time.

4. The apparatus of claim 1 wherein said normalization means further include means for calculating the standard deviation of successive values of one of the calculated ratios.

5. The apparatus of claim 1 further comprising in combination inhibiting means connected to said alarm signal generator means for preventing transmission of said alarm signal if the denominator of one of the ratios is decreasing, thereby causing the corresponding normalized ratio to exceed the threshold level.

6. The apparatus of claim 1 further comprising in combination:
    a sensor for detecting a variable other than carbon dioxide concentration and for producing an auxiliary electrical signal representative of the variable; and,
    inhibiting means connected to said alarm signal generator means and responsive to said auxiliary electrical signal for inhibiting transmission of said alarm signal when said auxiliary electrical signal has a certain value.

7. The apparatus of claim 6 wherein said variable other than carbon dioxide concentration is temperature.

8. The apparatus of claim 1 wherein said normalization means further comprise memory means for storing ratios calculated at past times.

9. The apparatus of claim 8 wherein said comparison means further comprise means for comparing current ratios with the stored ratios calculated at past times.

10. A method for detecting a fire in a room comprising the steps of:
   a) placing carbon dioxide sensors at spaced locations in the room, each of said sensors producing an electrical output signal representative of the concentration of carbon dioxide sensed in the air at its location;
   b) transmitting the electrical output signals generated by the sensors to a computer;
   c) calculating the ratio of the concentration sensed by each sensor to the concentration sensed by each of the other sensors;
   d) normalizing the calculated ratios;
   e) comparing each of the normalized ratios to a threshold level that is related in a known way to a desired false alarm rate;
   f) generating an alarm signal when any of the normalized ratios exceeds its threshold level.

11. The method of claim 10 wherein step a) further includes placing some of the carbon dioxide sensors at a different elevation from the other carbon dioxide sensors.

12. The method of claim 11 wherein step a) further includes placing some of the carbon dioxide sensors at a location near the ceiling of the room and others of the carbon dioxide sensors at a location near the floor of the room.

13. The method of claim 10 further comprising the additional step of inhibiting the alarm signal if the denominator of one of the ratios is decreasing, thereby causing the corresponding normalized ratio to exceed the threshold level.

14. The method of claim 10 further comprising the additional step of inhibiting the alarm signal in response to a signal from a sensor that is not a carbon dioxide sensor.

15. Apparatus for detecting a fire in a room, comprising in combination:
   at least two carbon dioxide sensors positioned at spaced locations in the room, each sensor producing an electrical output signal that represents the concentration of carbon dioxide sensed at the location of the sensor;
   normalization means electrically connected to said at least two carbon dioxide sensors for receiving the electrical output signals and for calculating normalized concentrations;
   comparison means for comparing the normalized concentrations to a threshold value that, in the absence of a fire, has only a pre-selected small probability of being exceeded by a normalized concentration; and,
   alarm signal generator means for generating an alarm signal when any of the normalized concentrations exceeds the threshold value.

16. The apparatus of claim 15 wherein some of said at least two carbon dioxide sensors are positioned at different elevations within the room.

17. The apparatus of claim 15 wherein said normalization means further include means for calculating the standard deviation of the concentrations sensed at a particular time.

18. The apparatus of claim 15 wherein said normalization means further include means for calculating the standard deviation of successive values of one of the sensed concentrations.

19. The apparatus of claim 15 further comprising in combination:
   a sensor for detecting a variable other than carbon dioxide concentration and for producing an auxiliary electrical signal representative of the variable; and,
   inhibiting means connected to said alarm signal generator means and responsive to said auxiliary electrical signal for inhibiting transmission of said alarm signal when said auxiliary electrical signal has a certain value.

20. The apparatus of claim 1 wherein said variable other than carbon dioxide concentration is temperature.

21. The apparatus of claim 15 wherein said normalization means further comprise memory means for storing concentrations sensed at past times.

22. The apparatus of claim 21 wherein said comparison means further comprise means for comparing current sensed concentrations with concentrations sensed at past times.

* * * * *